(12) United States Patent
Ducharme

(10) Patent No.: US 8,518,035 B2
(45) Date of Patent: Aug. 27, 2013

(54) ELECTROSURGICAL ROTATING CUTTING DEVICE

(75) Inventor: Richard W. Ducharme, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 480 days.

(21) Appl. No.: 12/644,951

(22) Filed: Dec. 22, 2009

(65) Prior Publication Data
US 2010/0160911 A1 Jun. 24, 2010

Related U.S. Application Data

(60) Provisional application No. 61/139,980, filed on Dec. 22, 2008.

(51) Int. Cl.
*A61B 18/18* (2006.01)

(52) U.S. Cl.
USPC .................................. 606/39; 606/45; 606/46

(58) Field of Classification Search
USPC ......................................... 606/39–42, 45–49
See application file for complete search history.

(56) References Cited

U.S. PATENT DOCUMENTS

| | | |
|---|---|---|
| 3,730,185 A | 5/1973 | Cook et al. |
| 4,311,143 A | 1/1982 | Komiya |
| 4,865,030 A | 9/1989 | Polyak |
| 5,024,617 A | 6/1991 | Karpiel |
| 5,075,062 A | 12/1991 | Karpiel |
| 5,241,970 A | 9/1993 | Johnlin, Jr. et al. |
| 5,490,836 A | 2/1996 | Desai |
| 5,601,582 A | 2/1997 | Shelton |
| 5,785,531 A | 7/1998 | Leung |
| 6,117,150 A | 9/2000 | Pingleton et al. |
| 6,533,782 B2 | 3/2003 | Howell et al. |
| 6,602,250 B2 | 8/2003 | Karpiel |
| 7,125,408 B2 | 10/2006 | Okada |
| 7,559,452 B2 | 7/2009 | Wales et al. |
| 2004/0039249 A1 | 2/2004 | Shiro et al. |
| 2004/0172018 A1* | 9/2004 | Okada ............................ 606/46 |
| 2004/0210284 A1 | 10/2004 | Okada |
| 2005/0215996 A1* | 9/2005 | Ouchi ............................ 606/46 |
| 2006/0178657 A1* | 8/2006 | Sugita et al. ..................... 606/1 |

(Continued)

FOREIGN PATENT DOCUMENTS

WO WO 00/42926 7/2000

OTHER PUBLICATIONS

International Search Report/Written Opinion for PCT/US2009/069258 (Mar. 3, 2010).

*Primary Examiner* — Linda Dvorak
*Assistant Examiner* — Brian M Antiskay
(74) *Attorney, Agent, or Firm* — Brinks Hofer Gilson & Lione

(57) ABSTRACT

An electrosurgical cutting device and method thereof for incising tissue are disclosed. The electrosurgical cutting device includes an asymmetrical cutting element that is affixed to a distal end of a torque cable. The cutting element is disposed within an end cap and is axially movable between a retracted position and an extended position. Rotation of the torque cable during a procedure allows the cutting element to rotationally align with and hook the target tissue onto the cutting element. An elongate member of the cutting element selectively lifts the target tissue away from surrounding tissue and structures. Having lifted the tissue away the surrounding tissue and structures, incision can occur.

17 Claims, 8 Drawing Sheets

(56) References Cited

U.S. PATENT DOCUMENTS

| | | |
|---|---|---|
| 2007/0250057 A1 | 10/2007 | Nobis et al. |
| 2007/0255299 A1 | 11/2007 | Vakharia et al. |
| 2007/0255303 A1 | 11/2007 | Bakos et al. |
| 2007/0255306 A1 | 11/2007 | Conlon et al. |
| 2007/0282327 A1 | 12/2007 | Muyari |
| 2008/0195094 A1 | 8/2008 | Okada |
| 2008/0269558 A1 | 10/2008 | Yahagi et al. |
| 2008/0275444 A1 | 11/2008 | Onishi |
| 2008/0281153 A1 | 11/2008 | Nakamura et al. |
| 2009/0005778 A1* | 1/2009 | Ducharme ............ 606/46 |
| 2009/0275967 A1 | 11/2009 | Stokes et al. |
| 2009/0306683 A1 | 12/2009 | Zwolinski et al. |
| 2010/0198244 A1 | 8/2010 | Spivey et al. |
| 2010/0198248 A1 | 8/2010 | Vakharia |

* cited by examiner

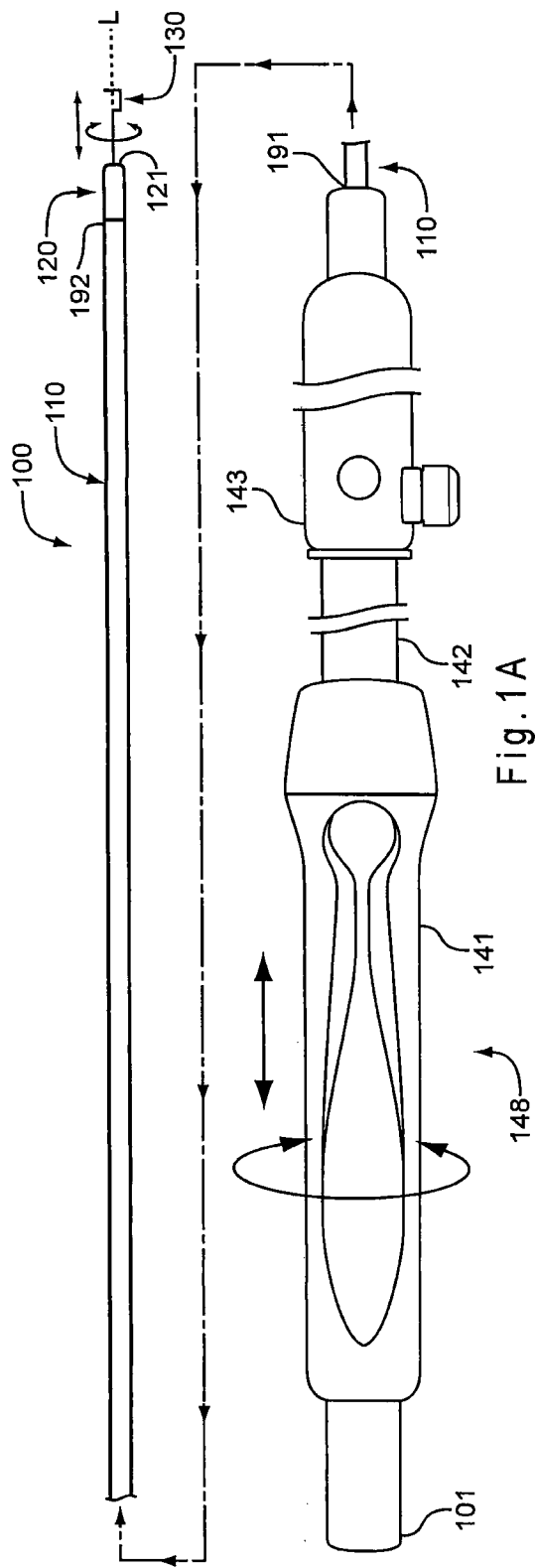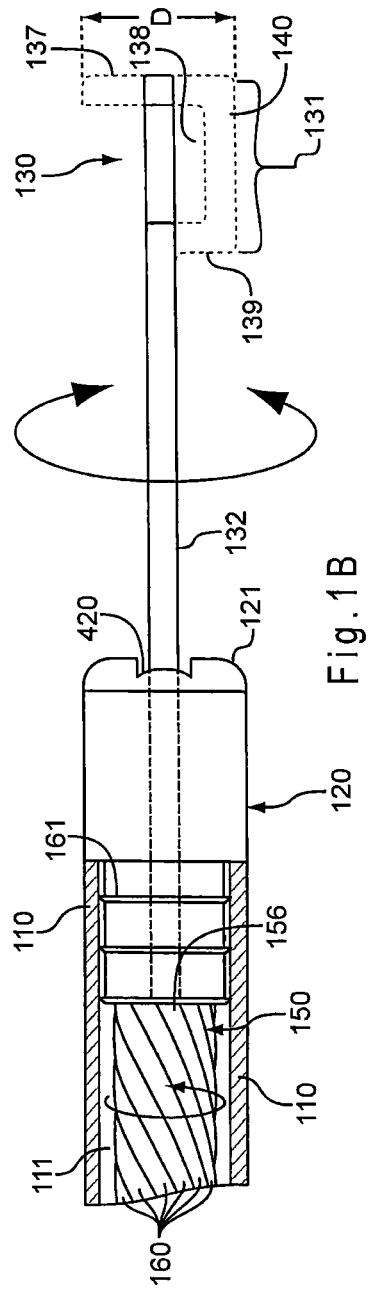
Fig.1A
Fig.1B

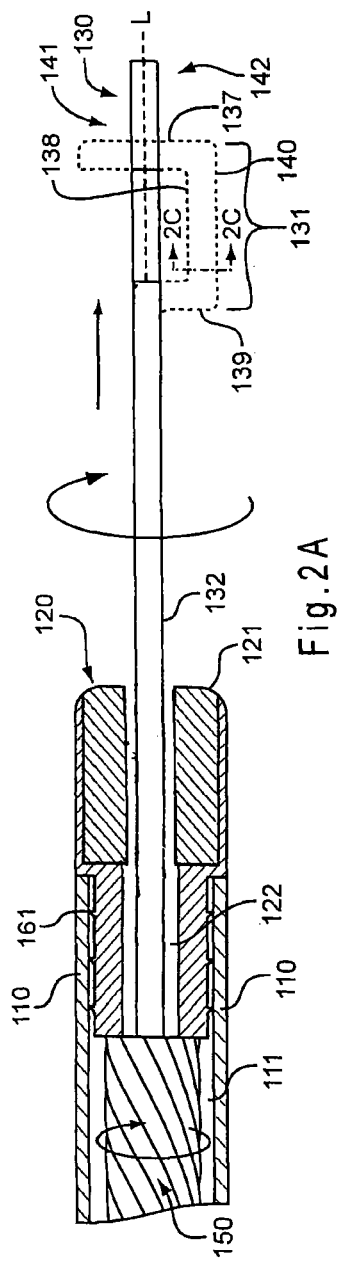
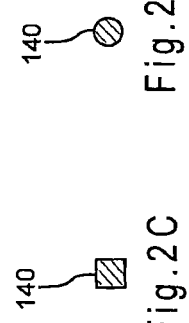
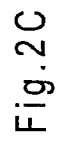
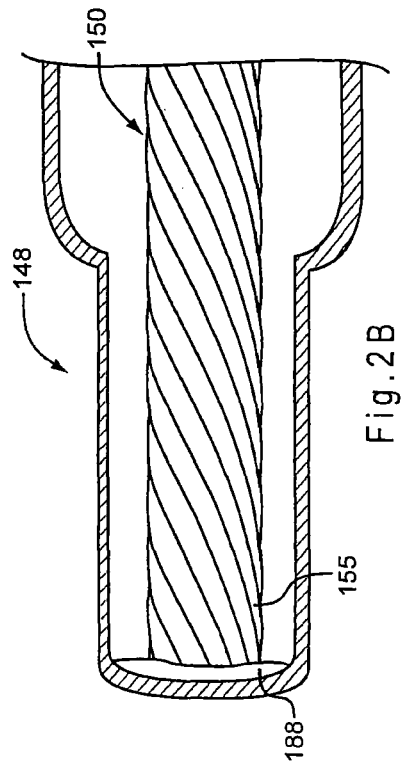

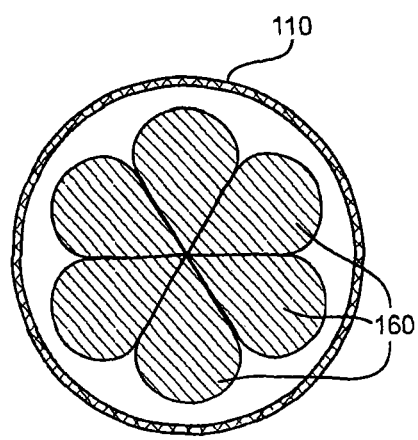 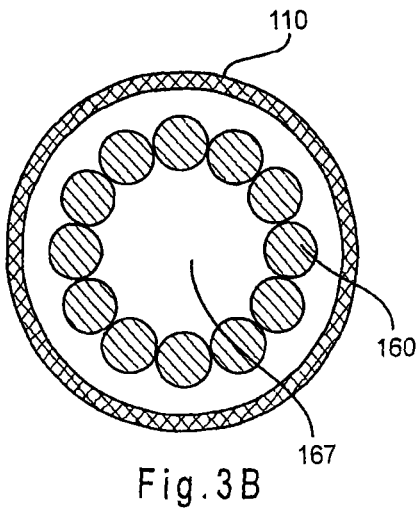
Fig.3A　　　Fig.3B
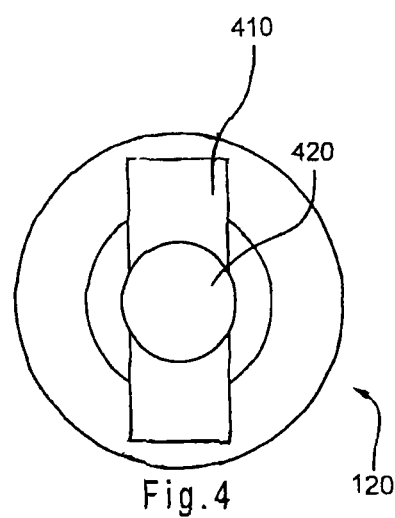
Fig.4

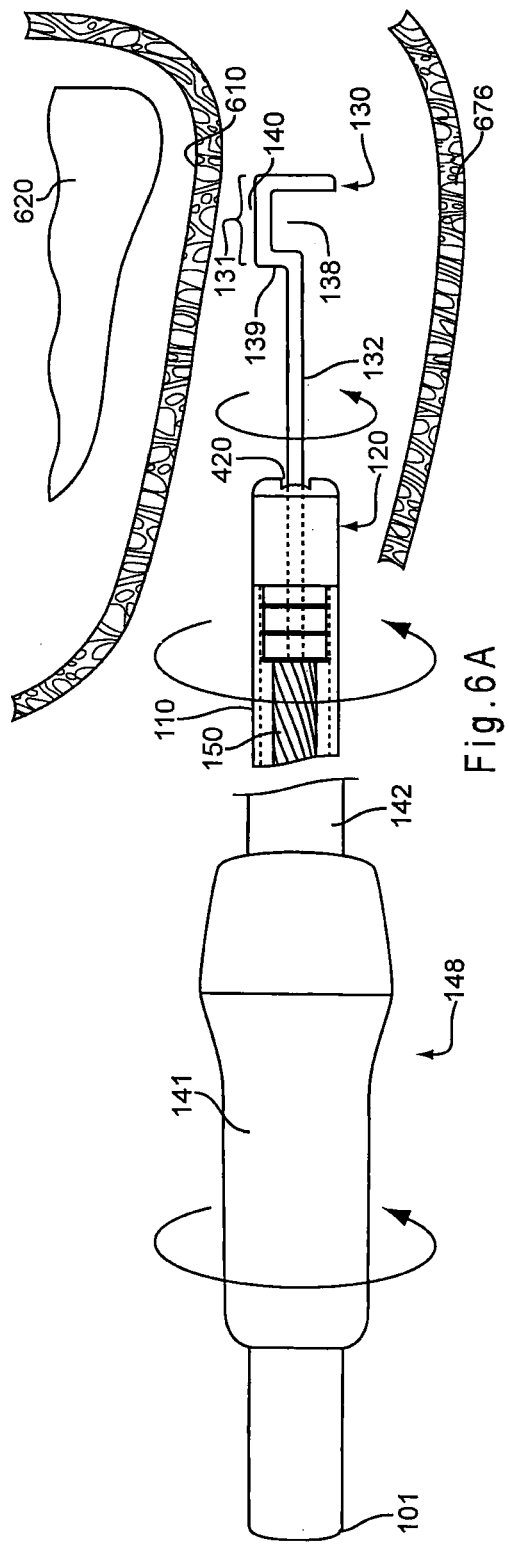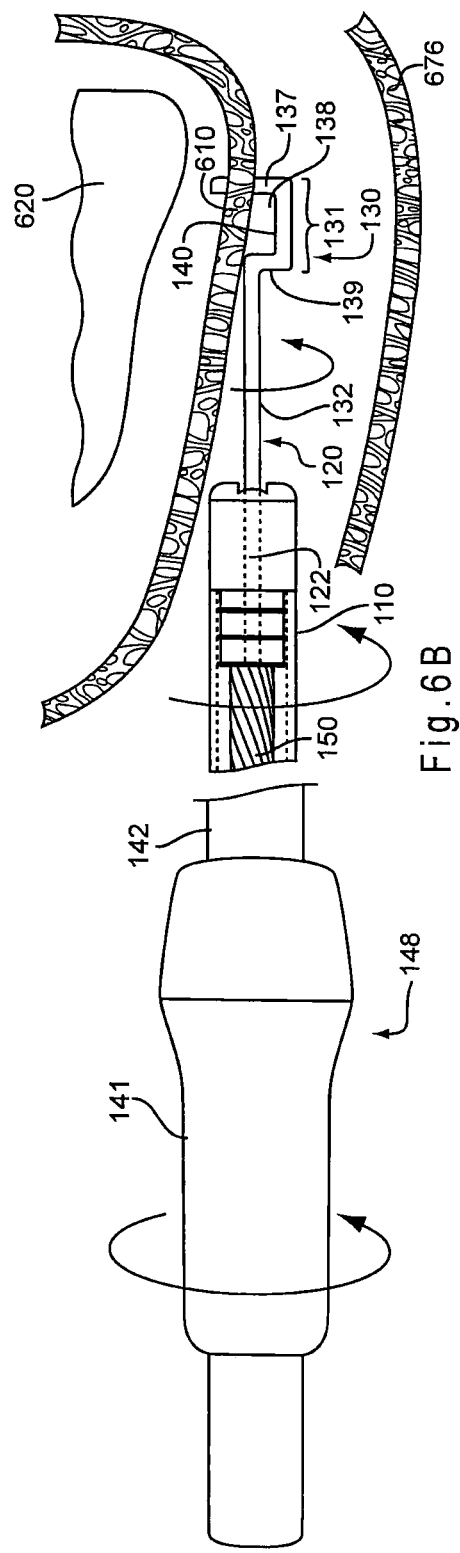

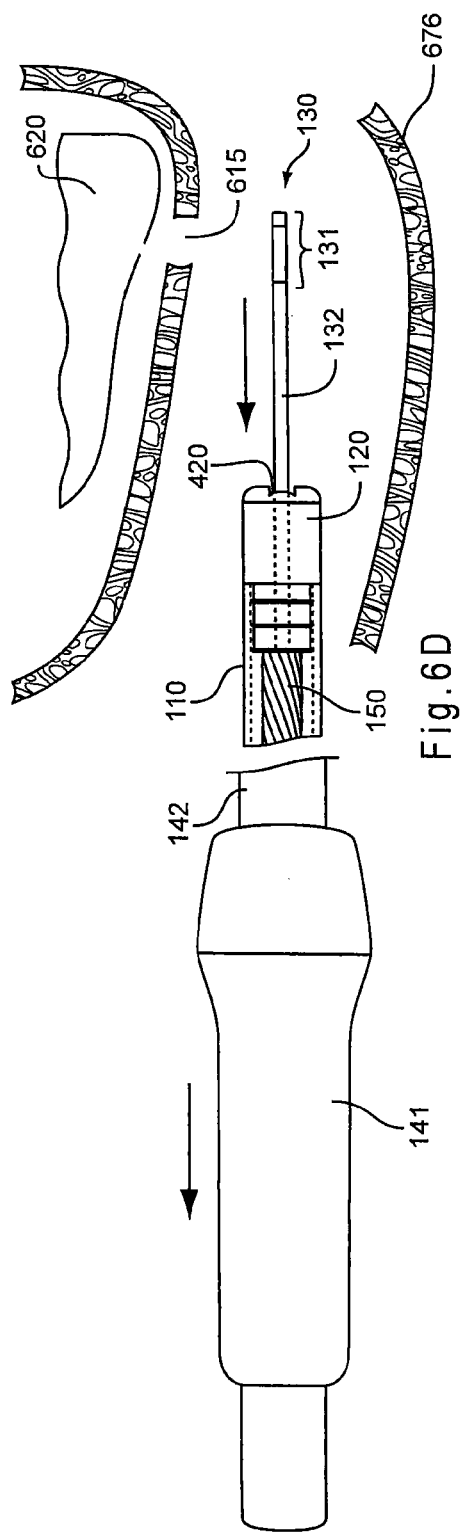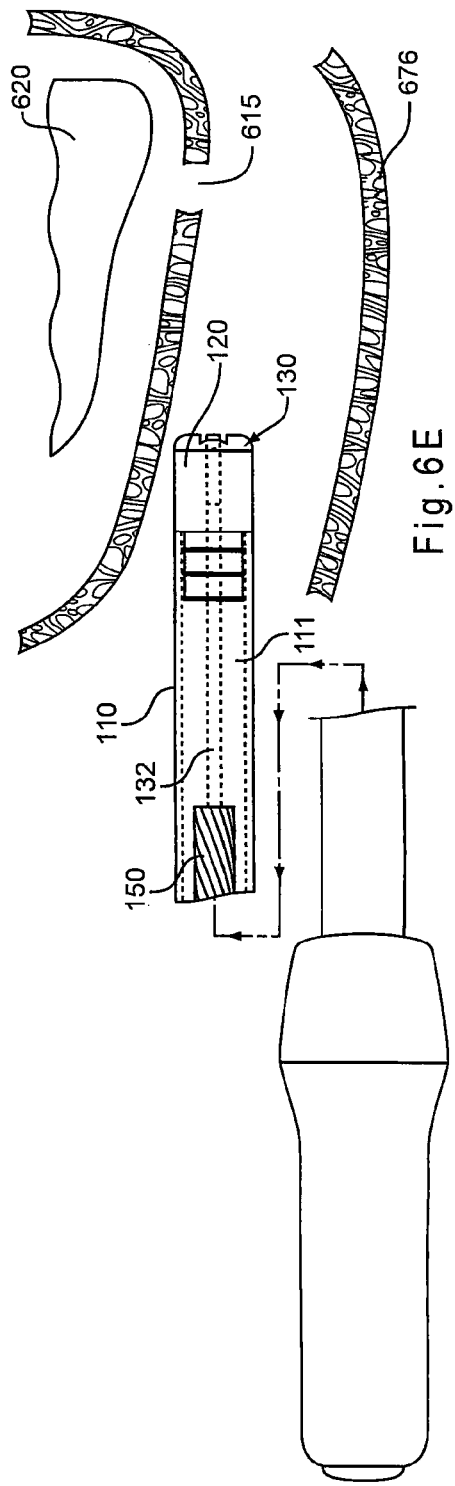

ELECTROSURGICAL ROTATING CUTTING DEVICE

CROSS-REFERENCE

This application claims the benefit of U.S. Provisional Application Ser. No. 61/139,980 filed on Dec. 22, 2008, entitled "ELECTROSURGICAL ROTATING CUTTING DEVICE," the entire contents of which are incorporated herein by reference.

BACKGROUND

Openings or perforations in the walls of internal organs and vessels may be naturally occurring, or formed intentionally or unintentionally. These openings may be used to gain access to adjacent structures of the body, such techniques being commonly referred to as transluminal procedures. For example, culdoscopy was developed over 70 years ago, and involves transvaginally accessing the peritoneal cavity by forming an opening in the cul de sac. This access to the peritoneal cavity allows medical professionals to visually inspect numerous anatomical structures, as well as perform various procedures such as biopsies or other operations, such as tubal ligation. Many transluminal procedures for gaining access to various body cavities using other bodily lumens have also been developed. Natural orifices such as the mouth, nose, ear, anus or vagina may provide access to such bodily lumens and cavities. The bodily lumen(s) of the gastrointestinal tract are often endoscopically explored and can be utilized to provide access to the peritoneal cavity and other body cavities, all in a minimally invasive manner. U.S. Patent Application No. 60/872,023 filed Feb. 28, 2007, discloses such a procedure, and is incorporated herein by reference in its entirety.

Compared to traditional open surgery or laparoscopic surgery, transluminal procedures are less invasive by eliminating abdominal incisions (or other exterior incisions) and incision related complications, while also reducing postoperative recovery time, reducing pain, and improving cosmetic appearance. At the same time, there remain challenges to transluminal procedures, including providing a suitable conduit to the openings and body cavities, robust medical devices that are maneuverable via the conduit and operable within the body cavity, sterility of the conduit, maintaining insufflation of the body cavity, proper closure of the opening and prevention of infection. For example, when an opening is formed in a bodily wall of the gastrointestinal tract, such as in the stomach or intestines, spillage of the stomach contents, intestinal contents or other bodily fluids into the adjacent body cavity can occur. Travel of bacteria laden fluids outside of the gastrointestinal tract may cause unwanted and sometimes deadly infection.

There is also the risk of perforating structures that lie just beyond the bodily wall being cut. For example, when incising the gastric wall, the potential of hitting blood vessels without knowing could lead to bleeding complications. Accidentally puncturing the small intestines could lead to the spillage of bacteria into the peritoneal cavity.

SUMMARY

The invention may include any of the following aspects in various combinations and may also include any other aspect described below in the written description or in the attached drawings.

In a first aspect, an electrosurgical cutting device is provided. The device comprises an outer elongate sheath having a proximal and a distal end with a central longitudinal axis therebetween. The sheath further comprises a lumen extending from the proximal end to the distal end. A torque cable is also provided comprising a plurality of metallic wires helically twisted about the central longitudinal axis of the outer elongate sheath to form a rope-like structure extending between a proximal end and a distal end. The torque cable extends within the lumen of the outer elongate sheath. An electrically conductive cutting element is also provided having a proximal portion attached to the distal end of the torque cable and configured to extend within the lumen of the sheath. The cutting element further has a distal portion that extends about a longitudinal axis of the cutting element, the cutting element configured to be rotationally and axially movable by a corresponding rotational and axial movement of the torque cable such that the cutting element selectively lifts target tissue onto a surface of the cutting element for incision.

In a second aspect, an electrosurgical cutting device is provided. An outer elongate sheath is provided having a proximal and a distal end with a central longitudinal axis therebetween. The sheath further comprises a lumen extending along the longitudinal axis. An end cap is also provided having a proximal portion and a distal portion, the proximal portion attached to the distal end of the outer elongate sheath and the distal portion comprising a slotted opening. The end cap further comprises a passageway in communication with the lumen of the sheath and the slotted opening of the distal portion of the cap. A torque cable is provided comprising a plurality of metallic wires helically twisted about the central longitudinal axis of the outer elongate sheath to form a rope-like structure extending between a proximal end and a distal end. The torque cable extends through the lumen of the outer elongate sheath. An electrically conductive hook having a proximal straight portion attaches to the distal end of the torque cable. The proximal straight portion of the hook is configured to extend within the passageway of the end cap and is substantially parallel to the central longitudinal axis of the outer elongate sheath. The hook further comprises a distal portion asymmetrically disposed about the central longitudinal axis, the hook configured to be rotationally and axially movable by a corresponding rotational and axial movement of the torque cable such that the rotational and axial movement of the cutting element causes the hook shape to selectively lift target tissue onto the hook for incision.

In a third aspect, a method for incising target tissue is provided. An electrosurgical cutting device is provided comprising an outer elongate sheath having a proximal and a distal end with a central longitudinal axis therebetween. The sheath further comprises a lumen extending from the proximal end to the distal end. A torque cable comprises a plurality of metallic wires, the cable extending within the lumen of the outer elongate sheath. An asymmetrical electrically conductive cutting element has a proximal portion attached to the distal end of the torque cable. The cutting element further has a distal portion that is asymmetrical about a longitudinal axis of the cutting element. The device is advanced towards the target tissue with the cutting element disposed in an axially retracted configuration. The cutting element is axially extended in a distal direction. The torque cable is rotated to correspondingly rotate the distal portion of the asymmetrical cutting element so as to rotationally align the distal portion of the asymmetrical cutting element towards the target tissue. The target tissue is engaged onto the distal portion of the asymmetrical cutting element. The target tissue is lifted away from surrounding tissue and structures. Electrical current is applied through the torque cable to the distal portion of the cutting element. Target tissue is incised.

BRIEF DESCRIPTION OF SEVERAL VIEWS OF THE DRAWINGS

The invention may be more fully understood by reading the following description in conjunction with the drawings, in which:

FIG. 1A shows a side view of an electrosurgical cutting device having an asymmetrical cutting element in an extended configuration;

FIG. 1B shows an expanded and partial cross sectional view of a distal portion of the electrosurgical cutting device of FIG. 1A, the distal portion including a torque cable disposed within an outer sheath and an end cap attached to the outer sheath, the outer sheath having an aperture through which the asymmetrical cutting element extends therethrough;

FIG. 2A shows a partial cross-sectional view of the distal portion of the cutting device of FIG. 1B in which the cutting element is rotated clockwise;

FIG. 2B shows the proximal portion of a control handle assembly attached to the torque cable;

FIG. 2C shows a rectangular cross-sectional shape of the cutting element;

FIG. 2D shows a circular cross-sectional shape of the cutting element;

FIG. 3A shows an end cross sectional view of the cutting device of FIG. 1 in which the torque cable is disposed within a lumen of the outer elongate sheath;

FIG. 3B shows an alternative cross sectional view of a torque cable disposed within the outer elongate sheath, the torque cable having a hollow opening;

FIG. 4 shows a distal end view of the slotted opening of the end cap;

FIG. 6A shows the cutting device having been advanced to a target tissue site of a bodily wall and the asymmetrical cutting element extended from the end cap, the cutting element thereafter rotated to be rotationally aligned with the target tissue;

FIG. 6B shows the cutting element having been rotated so as to engage the target tissue onto the hook portion of the cutting element and thereafter incise the target tissue;

FIG. 6D shows the tissue incised so as to create an access opening through the bodily opening with the hook portion of the cutting element thereafter rotated such that the vertical member of the hook portion is aligned with the slotted opening of the end cap;

FIG. 6E shows the proximal portion of the asymmetrical cutting element and hook portion entirely disposed within the end cap, the vertical member of the hook portion seated within the slotted opening.

DETAILED DESCRIPTION

Figure 5:
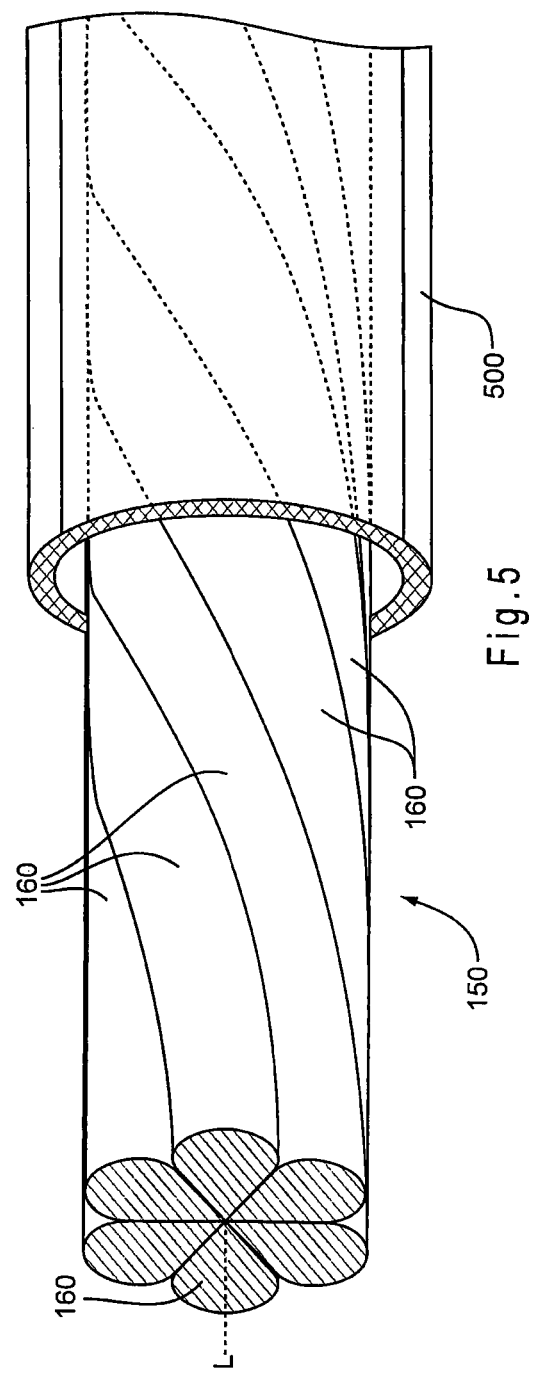
FIG. 5 shows an alternative embodiment in which a reinforcement member is disposed over the torque cable, the reinforcement member being designed to stabilize the cable during bending.

The terms "proximal" and "distal" as used herein are intended to have a reference point relative to the user. Specifically, throughout the specification, the terms "distal" and "distally" shall denote a position, direction, or orientation that is generally away from the user, and the terms "proximal" and "proximally" shall denote a position, direction, or orientation that is generally towards the user.

An exemplary electrosurgical rotating cutting device is shown in FIG. 1A. FIG. 1A is an exterior side view of an electrosurgical cutting device 100 for incising tissue. FIG. 1A shows that the exterior of the cutting device 100 generally includes a control handle assembly 148, an outer elongate sheath 110, an end cap 120, and an asymmetrical cutting element 130. The outer elongate sheath 110 has a proximal end 191 and a distal end 192. The proximal end 191 of the outer elongate sheath 110 is affixed to the handle assembly 148 and the distal end 192 is affixed to the end cap 120. The end cap 120 has an aperture 420 (FIG. 4) through which an asymmetrical electrically conductive cutting element 130 extends therethrough. The cutting element 130 is axially movable between a retracted position and an extended position. FIGS. 1A and 1B show that the cutting element 130 has been extended from the aperture 420 of the end cap 120 into the axially extended position, in which an asymmetrical distal portion 131 of the cutting element 130 extends beyond a distal end 121 of the end cap 120. The cutting element 130 incises tissue when oriented in the axially extended position. The cutting element 130 is also configured to retract into end cap 120, as shown in FIG. 6D, when the cutting element 130 is not utilized for incising tissue.

The cutting element 130 is also rotationally movable as will now be explained. FIG. 1B depicts an expanded and partial cross sectional view of a distal portion of the electrosurgical cutting device 100 of FIG. 1A. FIG. 1B shows that a torque cable 150 is disposed within a lumen 111 of the outer elongate sheath 110. The distal end 156 of the cable 150 is affixed to a proximal portion 132 of the cutting element 130, and the proximal end 155 of the torque cable 150 is affixed (e.g., soldered) to the control handle assembly 148, as shown in FIG. 2B. The cutting element 130 has a distal portion 131, which is asymmetrical about a central longitudinal axis L (FIG. 1A) of the device 100. FIG. 1B shows that the asymmetrical distal portion 131 rotates about 90 degrees in a counterclockwise rotation from the phantom line configuration to the solid line configuration. Because the handle assembly 148 is affixed to the cable 150, rotating the control handle assembly 148, as shown by the arrow in FIG. 1A, correspondingly causes the torque cable 150 to rotate, as shown by the arrow in FIG. 1B. Because the cable 150 is affixed to the cutting element 130, the rotation of the cable 150 correspondingly causes the cutting element 130 to undergo rotation in the same direction as the cable 150, as shown by the arrow about the cutting element 130 in FIG. 1B.

Referring to FIG. 2A, the asymmetrical distal portion 131 of the cutting element 130 comprises a first vertical member 139, a second vertical member 137, and a horizontal member 140 connecting the first vertical member 139 to the second vertical member 137. FIG. 2A shows that the second vertical member 137 has a greater lateral height than the first vertical member 139. In particular, FIG. 2A shows that the second vertical member 137 crosses over the central longitudinal axis L of the device 100 whereas the first vertical member 139 simply projects away from the central longitudinal axis L.

The axis L creates a lower area 142 and upper area 141, as defined by the orientation of FIG. 2A. Lower area 142 is defined as the region occupied below the central longitudinal axis L. Upper area 141 is defined as the region occupied above the central longitudinal axis L. First vertical member 139 is shown to be disposed in the lower area 142, and the second vertical member 137 is shown to span both the lower area 142 and the upper area 141. The second vertical member 137 is shown to have a lateral length D which is sized to fit within slotted opening 410 of the end cap 120. In the embodiment of FIG. 1B, the first vertical member 139 has a lateral length that may range from about 0.025 inches (0.635 mm) to 0.080 inches (2.032 mm), and the second vertical member 137 has a lateral length that may range from about 0.050 inches (1.27 mm) to 0.160 inches (4.064 mm). Other lateral lengths for first vertical member 139 and second vertical member 137 are contemplated. For example, the first vertical member 139 may cross the axis L so as to extend into the upper area 141 but still possess a shorter lateral length than that of the second vertical member 137. FIG. 2A shows the horizontal member 140 may be entirely disposed within the lower area 142 so as to connect an end of the first vertical member 139 to an end of the second vertical member 137 that is disposed within the lower area 142. The horizontal member 140 is preferably a sufficient longitudinal length to create a recessed opening 138 into which tissue may be engaged during an incision procedure.

Accordingly, the distal portion 131 depicted in FIGS. 1A, 1B, 2A, and 6A-6D is formed as a hook. The hook is spaced away from a central longitudinal axis L and is configured to rotationally and axially move by corresponding rotational and axial movement of the torque cable 150. The hook preferably includes an elongate vertical member 137 which traverses the central longitudinal axis L, as shown in FIG. 1B. The vertical member 137 preferably has a longitudinal length, denoted as "D" in FIG. 1B, that is at least equal to the thickness of the target tissue to be incised. Generally speaking, a larger vertical member 137 as denoted by "D" may help to achieve greater control and selectivity of incising target tissue. Additionally, having a vertical member 137 with such increased longitudinal length "D" may also enable more tissue to be incised. The length "D" of the vertical member 137 may be limited by various factors, including the need to maintain a lateral profile of the device 100 which is capable of being advanced within an accessory channel as well as the target region that device 100 is to be utilized within. Such competing factors may be taken into account when designing a suitable vertical length "D" for elongate vertical member 137. Determining a suitable length vertical member 137 for a particular application on the basis of such various factors will become apparent to one of ordinary skill in the art.

The asymmetrical distal portion 131 may possess numerous cross-sectional shapes. A cross-section of the horizontal member 140 of FIG. 2A is shown in FIG. 2C. FIG. 2C shows that the horizontal member 140, as well as both vertical members 137 and 139, possesses rectangular cross-sectional shapes. Other cross-sectional shapes are contemplated. As an example, FIG. 2D shows that each of the three members 137, 139, and 140 may have a circular cross-section. Aperture 420 is preferably designed to have an opening corresponding to the cross-sectional shape of members 137, 139, and 140.

One particular advantage of the asymmetrical distal portion 131 is its ability to selectively engage target tissue and lift it away from the surrounding area. Specifically, the asymmetrical distal portion 131 lifts target tissue away from other surrounding bodily structures prior to energizing the distal portion 131 during incision of the target tissue. As a result, inadvertent injury to the surrounding bodily structures is avoided.

Figure 6C:
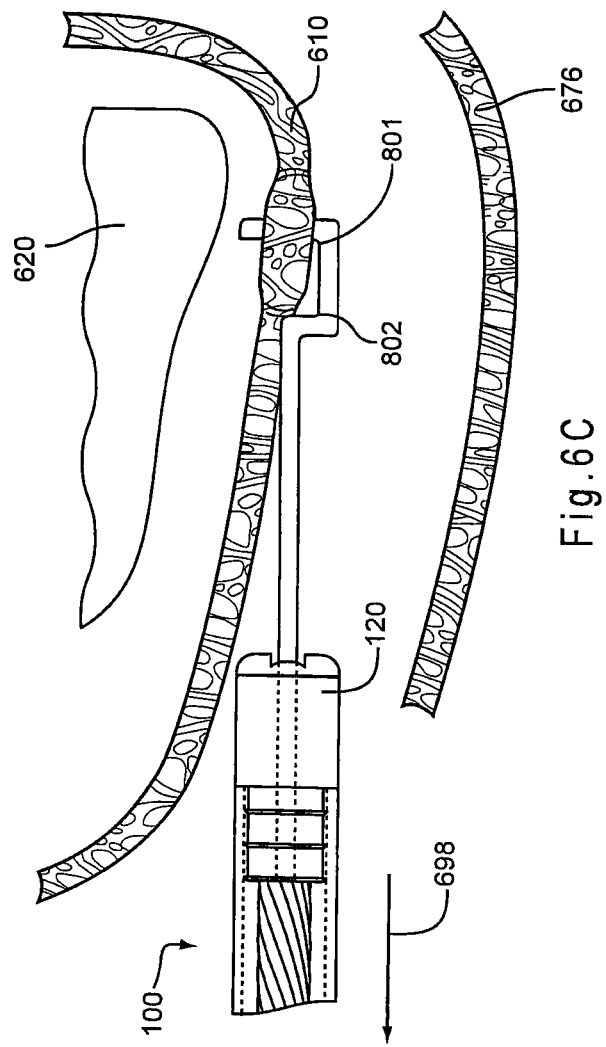
FIG. 6C is an expanded view of FIG. 6B showing a tissue strand hooked onto the hook and being lifted from out of the plane of the page.
Figure 7:
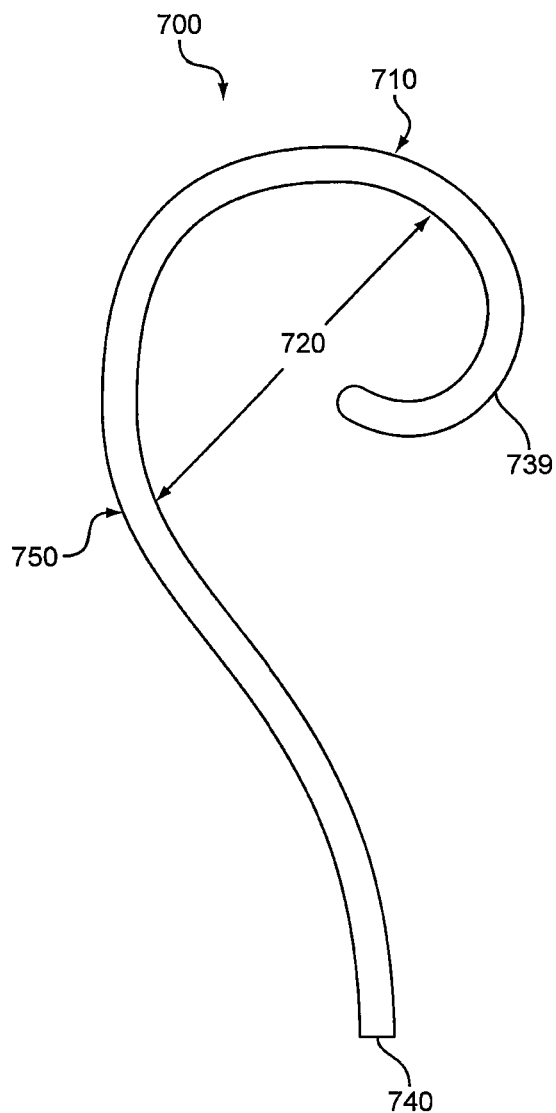
FIG. 7 shows a curvilinear hook.

Other types of shapes of the asymmetrical distal portion 131 are contemplated in addition to the hook-shape formed by at least the vertical member 137, and preferably the vertical member 139 and horizontal member 140 as well. The asymmetrical distal portion 131 may be other hook-shapes or asymmetrical shapes, including J-shaped, U-shaped, S-shaped, and question mark shaped. The distal portion 131 may also be polygonal shaped or curvilinear shaped. In one embodiment, the asymmetrical distal portion 131 is sickle shaped. FIG. 7 shows an example of a sickle shaped hook 700. The hook 700 includes a S-curved hook portion 739 which may penetrate tissue. The distal section includes a convex S-shaped portion which may facilitate lifting the tissue (FIG. 6C. The S-shaped hook 739 may also prevent the tissue from slipping off the hook 739 during incision of tissue. In particular, the convex section 710 is rounded outwards and extends backwards from the S-curved hook 739. The convex section 710 is sufficiently curved as shown to selectively lift or hook onto target tissue away from surrounding tissue and structures. Gap 720 is defined as the distance between the shank 750 and the convex section 710. The gap 720 is sufficiently sized for tissue to be captured therewithin. The S-curved hook 739 is shown not to be offset from shank 750. However, the S-curved hook 739 may be designed to be offset from the shank 750. The convex section 710 extends into a curved shank 750. The shank 750 extends to the base 740, which is affixed to distal end 156 of the cable 150.

The torque cable 150 is shown as a wire-stranded tubular structure in which each of several elements 160 is twisted along a helical axis. The cable 150 is preferably formed from a plurality of metallic wires 160 which are twisted to form a rope-like structure. A cross-section of the cable 150, as shown in FIG. 3a, shows that the wires 160 may converge with each other to create a solid structure. FIG. 3A shows that the rope-like cable structure is formed with six wire elements 160. Fewer than six or greater than six wire elements 160 are also contemplated for constructing the cable 150. FIG. 5 shows a perspective view of the cable 150 of FIG. 3A. It can be seen from FIG. 5 that the six wire elements 160 are twisted about central longitudinal axis L, with each of the wire elements 160 having a different helical pitch about axis L. A rope twisting machine as known in the art may be used to form the rope-like structure. Preferably, the absence of a gap between each of the wires 160 creates sufficient tightness. The rope twisting machine sufficiently compresses each of the elements 160 against one another to unite the wires 160 together such that the resultant rope-like cable 150 may not collapse.

Other design configurations for cable 150 are possible. For example, FIG. 3B shows that a plurality of wire elements 160 are twisted along a circular line into a hollow configuration 167. The cable 150 may also be braided such that the multiple wires 160 are intertwined similar to an interlaced yarn-like structure. A central wire could also be provided, around which the wire elements 160 are twisted or braided. Determining the precise type of cable 150 structure to use may be dependent upon numerous factors, including the allowable lateral profile of the device 100 for a particular application and the extent of torque transmissibility and responsiveness required for a particular application.

In a preferred embodiment, the cable 150 utilized in the device 100 is obtained from Asahi Intecc Co. The cable 150 may comprise an outer diameter ranging from about 0.30 mm to about 1.30 mm and include six (6) to eighteen (18) twisted wire elements 160, wherein each of the wire elements has a circular cross-sectional shape and is formed from stainless steel medical grade. The wire elements 160 may be circularly arranged and twisted to create a rope-like structure.

Referring back to FIG. 1B, FIG. 1B shows that the torque cable 150 extends within the lumen 111 of outer elongate sheath 110. The torque cable 150 provides flexibility and pushability, thereby allowing the device to 100 navigate within tortuous body lumens. The rope-like structure of the cable 150 enhances torque transmissibility and responsiveness. Specifically, rotating the proximal end 155 of the torque cable 150 via control handle assembly 148 causes the distal end 156 of the torque cable 150 to readily rotate in a controlled manner. In one embodiment, the cable 150 is designed with about a 1:1 torque transfer such that rotating the cable 15 degrees in a clockwise direction, for example, at the proximal end 155 of the control handle assembly 148 causes the distal end 156 of the cable 156 to also rotate about 15 degrees. In other embodiments, the ratio of torque transfer of the cable 150 may be adjusted by modifying the helical pitch (i.e., tightness of winding) of the wires 160 and the number of wires 160 such that rotating the cable 15 degrees in a clockwise direction, for example, at the proximal end 155 of the control handle assembly 148 causes the distal end 156 of the cable 156 to rotate greater than about 15 degrees. The ratio of torque transfer and transmissibility may be varied depending on the target region that electrosurgical cutting device 100 is introduced therewithin. To ensure smoothness of rotation of the cable 150, sufficient clearance exists between the outer diameter of the toque cable 150 and the inner diameter of the elongate sheath 110. The gap is illustrated in FIGS. 1b, 2b, 3a, 3b, and 6a-6d. In one example, the gap is about 0.005 inches (0.127 mm) or less.

FIG. 4 shows a cross-sectional end view of the slotted opening 410 of the end cap 120. The end cap 120 has a slotted opening 410 (FIG. 4) that is sized to receive the asymmetrical distal portion 131 of the cutting element 130. The end cap 120 also includes an aperture 420 that is sized to allow extension and retraction of proximal portion 132 of cutting element 130 therethrough. As depicted in FIG. 4, the slotted opening 410 is rectangular shaped, although the end cap 120 may have any shaped slotted opening that is adapted to receive the asymmetrical distal portion 131 of cutting element 130. Having the distal portion 131 of the cutting element 130 retract within opening 410 of the cap 120 reduces the lateral profile of the device 100, thereby facilitating advancement of the electrosurgical cutting device 100 to a target site and reducing trauma to a patient. The reduced lateral profile also helps to advance the electrosurgical cutting device 100 through an accessory channel of an endoscope during a procedure involving incision of tissue within the gastrointestinal tract, which will be explained in greater detail below.

The end cap 120 includes a passageway 122 (FIG. 2A) through which the proximal portion 132 (i.e. the stem) of the cutting element 130 can extend therethrough. The passageway 122 extends entirely through the longitudinal length of the end cap 120. The passageway is in communication with the lumen 111 of the outer elongate sheath 110 and the slotted opening 410 of the end cap 120.

The proximal end of the end cap 120 is shown in FIGS. 1B and 6A-6D to comprise ridges 161 which provide frictional engagement with the inner diameter of the outer elongate sheath 110. The outer diameter of the end cap 120 along the ridges 161 may be compression fit within the inner diameter of the outer elongate sheath 110 as shown in FIGS. 1B and 2A. Alternatively, or in addition, an adhesive may be utilized to secure the end cap 120 to the outer elongate sheath 110. The proximal end of the end cap 120 may be formed from any biocompatible material, preferably an electrically insulative material. The proximal end of cap 120 may also be formed from an electrically conductive material that is coated with an electrically insulative material. The end cap 120 may be designed end so that it is proportionate to the French size of the catheter which may range from about 3 Fr to about 15 Fr. The end cap 120 is preferably sized to have the same outer diameter as the outer elongate sheath 110 to create a smooth transition from outer elongate sheath 110 to the end cap 120, thereby creating an atraumatic end of the device 100.

Other means for affixing the end cap 120 to the distal end of the outer elongate sheath 110 are contemplated. In one embodiment, the end cap 120 and the elongate sheath 110 may be designed as a seamless part. For example, the end cap 120 may be injection molded over the elongate sheath 110, in a process known as over molding. The elongate sheath 110 is positioned within a mold such that hot polymer melt flows towards the distal end 192 of the sheath 110 and upon cooling and solidifying attaches to the distal end 192 of the outer elongate sheath 110. The resultant mold creates a fusion of the end cap 120 with the outer elongate sheath 110.

As mentioned, the cutting element 130 is electrically conductive and includes a proximal portion 132 and a distal portion 131. The proximal portion 132 extends from the distal portion 131 to the distal end 156 of the cable 150. The proximal portion 132 may be connected to the distal end 156 by adhesive, solder, or any other means known in the art. FIGS. 1B, 2A, and 6A-6D show that the proximal portion 132 of the cutting element 130 is disposed within the passageway 122 of end cap 120. The passageway 122 of the end cap 120 is preferably designed to have diameter which is sized smaller than the outer diameter of the cable 150. As a result, the cable 150 does not extend into passageway 122. The distal end 156 of cable 150 may abut against passageway 122, as shown in FIG. 1B, when the cutting element 130 is axially extended from the end cap 120. Such a configuration of the cable 150 abutted against passageway 122 represents the most axially extended position of cutting element 130. Thus, the cutting element 130 may only extend about 3 mm to about 15 mm from the distal end 192 of the sheath 110 and/or the distal end of end cap 120. The distal end 156 of cable 150 may be positioned proximal relative to this location, which is shown when the distal portion 131 of the cutting element 130 is axially retracted into slotted opening 410 of end cap 120, as shown in FIG. 6D.

As mentioned above, the distal portion 131 of cutting element 130 includes an asymmetrical cutting portion, which is responsible for incising tissue. The asymmetrical cutting portion is disposed asymmetrically about a longitudinal axis, L, (shown in FIG. 1A) of the device 100. The longitudinal axis L extends along the control handle assembly 148, the outer elongate sheath 110, the end cap 120, and the proximal portion 132 of the cutting element 130. The asymmetrical distal cutting portion 131 enables target tissue to be grabbed and lifted away from surrounding tissue and structures (e.g., artery), thereby avoiding inadvertent incision of the surrounding tissue and structures. Specifically, the asymmetrical distal portion 131 is preferably rotationally oriented so as to align the opening 138 (FIG. 1B) of the distal portion with the target tissue to be grabbed and lifted away from the surrounding tissue and structures.

The distal portion 131 is preferably made electrically conductive by an electrocautery unit (not shown) which supplies electrical energy. Monopolar current is preferably transmitted from the electrocautery unit through an electrical pin located at the proximal end 101 (FIG. 1A) of the device 100, through cable 150, and then to the surfaces of the distal portion 131. When the distal portion 131 contacts tissue, the current travels from the distal portion 131 into the tissue, thereby causing a current concentration at the interface of the distal portion 131 and tissue. Because the tissue acts like an electrical resistor, heat is generated along surfaces of distal portion 131 and thereafter is transferred to the tissue that the distal portion 131 is in contact with. The heat superheats the water that is naturally contained within the tissue cells, thereby causing the tissue cells to burst. This bursting of the tissue cells is a phenomenon commonly known in the art as electrosurgical cutting. The electrical current then continues to a grounding pad located on the patient's back. The current is then returned to the electrocautery unit.

There may be applications in which increased current density along the distal portion 131 may be desired. The current density at the interface of the distal portion 131 and tissue may be increased by insulating certain portions of the distal portion 131. In one example, portions of the distal portion 131 along its outside edges can be coated with an insulative coating, such as, for example Parylene®, which is commercially available from Uniglobe Kisco, Inc. Such an insulative coating has the effect of allowing electrocutting of tissue to occur only along the inside opening 138 (FIG. 1B) of the distal portion 131.

The distal portion 131 may be formed from a variety of materials, including any biocompatible and conductive metal or metallic alloy material which is sufficiently rigid to incise tissue and organs. Preferably, the distal portion 131 is formed from a rigid metallic alloy such as stainless steel of medical grade. The distal portion 131 may also be formed from a shape memory alloy, such as a nickel-titanium alloy.

Control handle assembly 148 includes stem 141 and spool 142, as shown in FIG. 1A. The spool 141 is slidably engaged with the stem 142. The spool 141 is provided with a range of slidable motion along the stem 142. Thus, axial movement of the spool 141 relative to the stem 142 causes the torque cable 150 and cutting element 130 attached thereto to correspondingly move in an axial direction relative to outer elongate sheath 110. Such axial movement is indicated by the dual linear arrows placed along the spool 141 and the cutting element 130 in FIG. 1A. Rotational movement of the spool 141 relative to the stem 142 causes the torque cable 150 and cutting element 130 to correspondingly move in a rotational direction relative to outer elongate sheath 110. Such rotational movement is indicated by the dual rotational arrows placed about the spool 141 and the cutting element 130 in FIG. 1A. FIG. 1A shows that the control assembly 140 further includes a stopper 143. The stopper 143 is adjustable along the stem 142. Tightening the stopper 143 along the stem at a predetermined axial position ensures that the spool 141 does not axially extend beyond the predetermined distance during a particular procedure. It should be understood that other configurations of the control handle assembly 148 can be employed to actuate the torque cable 150 and cutting element 130.

In an alternative embodiment, the toque cable 150 may include an outer stabilizing sheath 500, as shown in FIG. 5. The sheath 500 may be disposed over the torque cable 150 and within outer elongate sheath 110. The sheath 500 preferably extends the entire length of the torque cable 150. The sheath 500 is formed from a material that is more rigid relative to the outer elongate sheath 110 to stabilize the cable 150 and prevent it from substantial kinking during bending of the device 100. Preferably, the material has a thinner wall thickness than the outer elongate sheath 110 so as to not substantially increase the overall lateral profile of the device 100. One example of such a suitable material for sheath 500 is polyetheretherketone (PEEK). Other materials which are known in the art to be relatively rigid compared to outer elongate sheath 110 may also be used. The outer elongate sheath 110 is preferably formed from a flexible material having sufficient pushability to navigate device 100 through tortuous body lumens.

The device 100 may be used in various procedures. One exemplary method of using the electrosurgical device 100 will now be described with reference to FIGS. 6A-6E. FIGS. 6A-6E generally describe a technique for cutting away a target strand of tissue 610 that is covering target organ 620 without inadvertent incision of an unintended target 676, such as an artery. The tissue strand 610 may be omental adhesions, which are typically a collagenous, fibrous material that grow around the target organ 620 after a surgical procedure involving the organ 620. It should be understood that the unintended target 676 may also include other blood vessels, tissues or organs.

An endoscope is advanced through an esophagus and into the gastrointestinal tract of a patient until having reached a position within the stomach wall. The electrosurgical device 100 is advanced through an accessory channel of the endoscope with the asymmetrical hook distal portion 131 of cutting element 130 disposed within slotted opening 410 of end cap 120. An example of such a configuration is shown in FIG. 6D. Complete retraction of cutting element 120 within end cap 120 creates a reduced lateral profile of device during advancement through accessory channel of the endoscope.

The proximal end 101 of the handle assembly 148 is advanced beyond a distal end of the accessory channel until reaching the position shown in FIG. 6A. Having reached the location of the target strand of tissue 610, the cutting element 130 moves from its axially retracted position to its axially extended position by pushing spool 141 in a distal direction along stem 142 while pulling stem 142 of the control handle assembly 148. The extent to which the cutting element 130 axially extends may be controlled by fixating stopper element 143 (FIG. 1A) at a desired position along the stem 142. Note that for purposes of clarity, the stopper element 143 has been omitted from FIGS. 6A-6D. FIG. 6A shows that the asymmetrical distal hook portion 131 of cutting element 130 axially extends towards the target tissue strand 610. A predetermined portion of the proximal portion 132 of cutting element 130 emerges through aperture 420 of end cap 120. In the example shown in FIG. 6A, the distal end 156 of the cable 150 is shown abutted against the proximal end of the end cap 120, thereby representing the maximum axially extended position of the asymmetrical distal portion 131.

Because the opening 138 of the asymmetrical distal portion 131 is not yet facing the target tissue 610, rotational alignment of the opening 138 of the asymmetrical distal portion 131 with the tissue 610 may be necessary so as to enable hooking the tissue 610 onto the asymmetrical distal portion 131. Accordingly, the spool 141 is rotated in a counterclockwise direction about 180 degrees relative to the outer elongate sheath 110 and end cap 120, both of which remain substantially stationary during the rotation of the spool 141. The rotation is indicated in FIG. 6A by the counterclockwise rotational arrow about the spool 141. Rotation of the spool 141 causes torque cable 150 to correspondingly rotate in a counterclockwise direction, as indicated in FIG. 6A. The cable 150 transmits sufficient torque to proximal portion 132 and distal hook portion 131 of cutting element 130, thereby causing corresponding rotation of the cutting element 130, as indicated by the counterclockwise rotational arrow about the cutting element 130.

FIG. 6B shows that the asymmetrical distal portion 131 of the cutting element 130 is configured such that the opening 138 of the asymmetrical distal portion 131, as defined by horizontal member 140 connecting the first and the second vertical members 139 and 137, is now rotationally aligned and facing the target tissue 610 to be incised. At this point, the asymmetrical distal portion 131 engages (i.e., hooks) the target tissue strand 610 (FIG. 6B) such that target tissue strand 610 is secured at the opening 138 of asymmetrical distal portion 131 between the first and the second vertical members 139 and 137.

Having grasped or hooked the target tissue strand 610 onto asymmetrical distal portion 131, incision may begin. FIG. 6C is an expanded view of FIG. 6B, showing the tissue strand 610 hooked within opening 138 and onto the asymmetrical distal portion 131. The user grasps the control handle assembly 148 causing the device 100 to be pulled in a proximal direction towards a distal end of the endoscope as indicated by arrow 698. As the device 100 is pulled, asymmetrical distal portion 131 exerts a tensile force on the target tissue strand 610 so as to lift the tissue 610 out of the plane of the page. Preferably, the device 100 is pulled in the proximal direction at an angle to sufficiently maintain tissue 610 within opening 138 of asymmetrical distal portion 131, thereby preventing slippage and disengagement of tissue 610 from the asymmetrical distal portion 131. Pulling at a slight angle may ensure that tissue 610 remains at one of the inner corners 801 and 802 of the asymmetrical distal portion 131 (FIG. 6C). The tissue 131 continues to be lifted out of the plane of the page until sufficiently spaced apart from target organ 620 and unintended target 676.

Having lifted the tissue 610 sufficiently away from the target organ 620 and the unintended target 676, the asymmetrical distal portion 131 is energized for subsequent incision to occur. Electrical current is transmitted from an electrocautery unit, to electrical pin located at proximal end 101 of handle assembly 148, through the cable 150, and thereafter along exposed surfaces of the asymmetrical distal portion 131 to incise the tissue 610, as shown in FIG. 6C. During the incision, the device 100 may be maneuvered so that the tissue 610 can further advance into the opening 138 of asymmetrical distal portion 131 by pulling device 100 in the proximal direction at an angle, as mentioned above. The tissue strand 610 eventually is incised at location 615 (FIG. 6d) into two smaller strands. The incision of strand 610 creates smaller strands, thereby allowing subsequent access to target organ 620. The above procedure may be repeated numerous times to remove other tissue strands which may be covering target organ 620.

Because conventional needle knife devices push into the target tissue they incise, there may be a significantly higher risk of pushing forward towards the target organ 620 or the unintended target 676. A conventional electrosurgical needle knife typically incises with the side of the cutting wire as opposed to the distal end of the wire. As the side of the wire incises, it bends in a bow-like direction and pushes towards the target tissue, thereby compressing the target tissue towards any tissue or structures behind it. When the cut of the target tissue is complete, the wire straightens out in a whip like uncontrollable manner and may hit any tissue or structures behind the target tissue (i.e., the wire hits the target tissue 620 if the needle knife wire is cutting from right to left or the wire hits the unintended target 676 if the needle knife is cutting from left to right). This risk is avoided with the asymmetrical distal portion 131 because the incision occurs only after the tissue 610 has been sufficiently lifted away from the surrounding organ 620 and unintended target 676.

Having incised a sufficient number of strands to create an access to a target organ 620, the asymmetrical distal portion 131 may be retracted into the slotted opening 420 of the end cap 120. FIG. 6B shows that the that the spool 141 is rotated in a counterclockwise direction about 90 degrees in a counterclockwise direction relative to the outer elongate sheath 110 and end cap 120, both of which remain substantially stationary during the rotation of the spool 141. The rotation is indicated in FIG. 6B by the counterclockwise rotational arrow about the spool 141. Rotation of the spool 141 causes torque cable 150 to correspondingly rotate in a counterclockwise direction, as indicated in FIG. 6B. The cable 150 transmits sufficient torque to proximal portion 132 and asymmetrical distal portion 131 of cutting element 130, thereby causing corresponding rotation of the cutting element 130, as indicated by the counterclockwise rotational arrow about the cutting element 130. The spool 141 may alternatively be rotated about 90 degrees in a clockwise direction to rotate cable 150 and asymmetrical distal portion 131. Either direction of rotation enables the elongate vertical member 137 of the asymmetrical distal portion 131 to become vertically aligned with the slotted opening 410 of end cap 120 (FIG. 4).

FIG. 6D also shows the asymmetrical distal portion 131 rotated about 90 degrees counterclockwise to vertically align vertical member 137 within the slotted opening 410 of the end cap 120. With vertical member 137 aligned with slotted opening 410 (FIG. 4), the asymmetrical distal portion 131 may be retracted into end cap 120. FIG. 6C shows that the spool 141 is proximally retracted along stem 142. This may be achieved by pulling spool 141 while pushing stem 142. The proximal portion 132 reenters aperture 420 of end cap 120. Spool 141 continues to be retracted such that cable 150 is proximally retracting within the lumen 111 of outer elongate sheath 122 as shown in FIG. 6D. The spool 141 stops retracting when the vertical member 137 seats within the slotted opening 410 (FIG. 6D).

FIG. 6E shows the retracted orientation of the asymmetrical distal portion 131 completely disposed within slotted opening 410 of the end cap 120. Proximal portion 132 extends through passageway 122 of end cap 120 and into lumen 111 of outer elongate sheath 110. Having retracted the asymmetrical distal portion 131 into the end cap 120, the device 100 may be withdrawn from the patient. Numerous medical devices may thereafter be introduced towards the target organ 620 to conduct a procedure therein.

The above procedure may also be used to dissect a target organ away from another organ, such as the gallbladder away from the liver. A long sheet of collagenous membrane interconnects the gallbladder to the liver. The device 100 may be utilized to incise the membrane sheet without inadvertently cutting into an unintended area. The asymmetrical distal portion 131 initially tears a hole along a distal end of membrane sheet. Having anchored the asymmetrical distal portion 131 through the hole, the asymmetrical distal portion 131 is pulled back as described above to cut the membrane and allow separation of the gallbladder from the liver for subsequent procedures. The device 100 is advantageous over a conventional needle knife, which may accidentally puncture one of the organs as the knife wire is pushed in a distal direction into the membrane sheet. When the needle knife has completed cutting the membrane sheet, the wire straightens out in a whip like uncontrollable manner and may hit the gallbladder or the liver. Such a risk is substantially avoided with device 100.

Additionally, the device 100 may also be used for intraluminal procedures. In one example, the device 100 may be used for endoscopic mucosal resections, which involves removing cancerous tissue from flaps of tissue disposed along the stomach wall.

Having described the various components of the electrosurgical device 100, one exemplary method for assembling the components will now be discussed. The distal end 156 of the cable 150 is affixed to the proximal portion 132 of cutting element 130 to create the cutting element 130-cable 150 assembly. After securing the cutting element 130 to the cable 150, the proximal end 155 of the cable 150 is pulled in through aperture 420 of end cap 120. Next, an optional stabilizing sheath 500 may be slidably disposed over the cable 150. Outer elongate sheath 110 is slidably disposed over the cutting element 130-cable 150 assembly and optional stabilizing sheath 500. The ridges 161 of end cap 120 are then compression fitted with use of an adhesive within the outer elongate sheath 110. Control handle assembly 148 is then affixed to the proximal end 191 of outer elongate sheath 110. The handle assembly 148 may be secured to the proximal end of the torque cable 150 by solder 188, as shown in FIG. 2B. An electrical pin (not shown) is located at the proximal end 101 (FIG. 1A) of the handle assembly 148 and is configured to connect to an electrocautery generator unit (not shown) by an electrical cable. Having the electrical pin located along the proximal end 101 of the torque cable 150 allows the electrical cable to rotate along the longitudinal length of the torque cable 150 without the electrical cable undesirably tangling up with a user's hands during rotation of the handle assembly 148.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

The invention claimed is:

1. An electrosurgical cutting device comprising:
    an outer elongate sheath having a proximal and a distal end with a central longitudinal axis therebetween, the sheath further comprising a lumen extending from the proximal end to the distal end;
    a torque cable comprising a plurality of metallic wires helically wound about the central longitudinal axis of the outer elongate sheath to form a rope-like structure extending between a proximal end and a distal end, the torque cable extending within the lumen of the outer elongate sheath;
    an electrically conductive cutting element having a proximal portion attached to the distal end of the torque cable and configured to extend within the lumen of the sheath, the cutting element further having a distal portion that extends about a longitudinal axis of the cutting element, the cutting element configured to be rotationally and axially movable by a corresponding rotational and axial movement of the torque cable such that the cutting element selectively lifts target tissue onto a surface of the cutting element for incision, the cutting element being asymmetrical about the longitudinal axis; and
    an end cap having a proximal portion and a distal portion, the proximal portion attached to the distal end of the outer elongate sheath and the distal portion comprising a slotted opening, the slotted opening elongated in a direction transverse to the central longitudinal axis, the end cap further comprising a passageway in communication with the lumen of the sheath and the slotted opening of the distal portion of the cap, wherein, when the distal portion of the cutting element is positioned outside of the slotted opening, the cutting element rotates relative to the end cap between a first position where the asymmetrical cutting element is aligned with the slotted opening such that the cutting element may axially pass therethrough, and a second position where the asymmetrical cutting element is misaligned with the slotted opening such that the cutting element cannot axially pass therethrough, the elongated slotted opening sized to allow the entire cutting element to pass longitudinally therethrough.

2. The electrosurgical cutting device of claim 1, the distal portion of the cutting element further comprising a first vertical member, a second vertical member, and a horizontal member connecting the first and the second vertical members, wherein the first, the second, and the horizontal members are configured such that the distal portion is asymmetrical about a longitudinal axis of the cutting element.

3. The electrosurgical cutting device of claim 2, wherein the second vertical member has a lateral length greater than or equal to the first vertical member.

4. The electrosurgical cutting device of claim 2, wherein the lateral length of the first vertical member is between about 0.635 mm to about 2.032 mm, and the lateral length of the second vertical member is between about 1.27 mm to about 4.064 mm.

5. The electrosurgical cutting device of claim 2, wherein the device is axially movable between an axially retracted position and an axially extended position, wherein the axially retracted position is defined by the distal portion of the cutting element disposed within the slotted opening of the end cap and the axially extended position is defined by the distal portion of the cutting element extending beyond the distal portion of the end cap, the second vertical member in the axially extended position being configured to selectively lift the target tissue onto the cutting element.

6. The electrosurgical cutting device of claim 1, further comprising a control handle assembly operably connected to the proximal end of the torque cable, the control handle assembly comprising a stem and a spool slidably attached to the stem, the spool configured to axially slide in a first axial direction relative to the stem to cause the torque cable and the cutting element to axially move in the first axial direction.

7. The electrosurgical cutting device of claim 6, wherein the spool is configured to rotate in a first rotational direction relative to the stem to cause the torque cable and the cutting element to rotate in the first rotational direction.

8. The electrosurgical cutting device of claim 1, wherein the cable is separated from the outer elongate sheath by about 0.127 millimeters.

9. The electrosurgical cutting device of claim 2, wherein the asymmetrical distal portion is hook-shaped.

10. The electrosurgical cutting device of claim 2, wherein the asymmetrical distal portion is S-shaped.

11. The electrosurgical cutting device of claim 2, wherein the asymmetrical distal portion of the cutting element further comprises an electrically insulative layer of material along at least a portion of a surface of the cutting element.

12. The electrosurgical cutting device of claim 2, further comprising a sheath disposed over the torque cable to stabilize the cable during bending, the sheath comprising a material being more rigid relative to the outer elongate sheath.

13. The electrosurgical cutting device of claim 2, wherein the cutting element defines a laterally facing opening into which the tissue may be lifted.

14. A method for incising target tissue, comprising the steps of:
    (a) providing an electrosurgical cutting device comprising:
    an outer elongate sheath having a proximal and a distal end with a central longitudinal axis therebetween, the sheath further comprising a lumen extending from the proximal end to the distal end;
    an end cap having a proximal portion and a distal portion, the proximal portion attached to the distal end of the outer elongate sheath and the distal portion comprising a slotted opening, the slotted opening elongated in a direction transverse to the central longitudinal axis, the end cap further comprising a passageway in communication with the lumen of the sheath and the slotted opening of the distal portion of the cap;

a torque cable comprising a plurality of metallic wires, the cable extending within the lumen of the outer elongate sheath; and an asymmetrical electrically conductive cutting element having a proximal portion attached to the distal end of the torque cable, the cutting element further having a distal portion that is asymmetrical about a longitudinal axis of the cutting element and positioned within the endcap in an axially retracted configuration, wherein the elongated slotted opening is sized to allow the entire cutting element to pass longitudinally therethrough;

(b) advancing the electrosurgical cutting device towards the target tissue with the cutting element disposed in the axially retracted configuration;

(c) axially extending the cutting element in a distal direction beyond the endcap;

(d) rotating the torque cable to correspondingly rotate the distal portion of the asymmetrical cutting element so as to rotationally align the distal portion of the asymmetrical cutting element towards the target tissue;

(e) engaging the target tissue onto the distal portion of the asymmetrical cutting element;

(f) lifting the target tissue away from surrounding tissue and structures;

(g) applying electrical current through the torque cable to the distal portion of the cutting element; and (h) incising the target tissue.

15. The method of claim 14, wherein step (c) further comprises slidably extending a spool relative to a stem to axially extend the cutting element in the distal direction, wherein one of the stem and the spool is operably connected to the torque cable.

16. The method of claim 14, wherein step (d) further comprises rotating a spool relative to a stem to rotate the spool relative to the outer elongate sheath, wherein one of the stem and the spool is operably connected to the torque cable.

17. The method of claim 14, wherein step (f) further comprises pulling on a proximal end of the device so as to cause the asymmetrical cutting element to lift the target tissue away from the surrounding tissue and structures.

\* \* \* \* \*